(12) United States Patent
Zhu

(10) Patent No.: US 9,426,997 B2
(45) Date of Patent: Aug. 30, 2016

(54) THICKENING GLYPHOSATE FORMULATIONS

(75) Inventor: Shawn Zhu, Stormville, NY (US)

(73) Assignee: AKZO NOBEL N.V., Arnhem (NL)

( * ) Notice: Subject to any disclaimer, the term of this patent is extended or adjusted under 35 U.S.C. 154(b) by 384 days.

(21) Appl. No.: 13/059,449

(22) PCT Filed: Aug. 17, 2009

(86) PCT No.: PCT/EP2009/060588
§ 371 (c)(1),
(2), (4) Date: Feb. 17, 2011

(87) PCT Pub. No.: WO2010/020599
PCT Pub. Date: Feb. 25, 2010

(65) Prior Publication Data
US 2011/0210028 A1    Sep. 1, 2011

Related U.S. Application Data

(60) Provisional application No. 61/090,010, filed on Aug. 19, 2008.

(30) Foreign Application Priority Data

Sep. 9, 2008 (EP) ..................... 08163910

(51) Int. Cl.
*A01N 57/20* (2006.01)
*A01N 25/30* (2006.01)

(52) U.S. Cl.
CPC .............. *A01N 57/20* (2013.01); *A01N 25/30* (2013.01)

(58) Field of Classification Search
CPC ............................. A01N 57/20; A01N 25/30
USPC ........................................ 504/206
See application file for complete search history.

(56) References Cited

U.S. PATENT DOCUMENTS

| 5,317,003 A * | 5/1994 | Kassebaum et al. .......... 504/206 |
| 6,365,551 B1 | 4/2002 | Wright et al. |
| 6,838,415 B1 | 1/2005 | Muller et al. |
| 2003/0104943 A1 * | 6/2003 | Lennon et al. ................ 504/206 |
| 2005/0130842 A1 | 6/2005 | Fleute-Schlachter et al. |

FOREIGN PATENT DOCUMENTS

| CA | 2 581 340 C | 5/2014 |
| EP | 0 290 416 A2 | 11/1988 |
| EP | 1 202 623 B1 | 9/2004 |
| EP | 1 343 375 B1 | 8/2006 |
| RU | 2 250 902 C2 | 7/2003 |
| WO | WO 96/32839 | 10/1996 |
| WO | 99/62338 A1 | 12/1999 |
| WO | WO 00/15037 | 3/2000 |
| WO | 01/17358 A1 | 3/2001 |
| WO | 03/063589 A2 | 8/2003 |
| WO | WO 2006/034459 A1 | 3/2006 |
| WO | WO 2007/109791 A2 | 9/2007 |

OTHER PUBLICATIONS

European Search Report for Application No. 08163910.6: Completion Date Feb. 5, 2009.
International Search Report for Application No. PCT/EP2009/060588: Completion Date Nov. 11, 2010.
Wyrill et al., "Glyphosate toxicity to common milkweed and hemp dogbane as influenced surfactants," Weed Science, vol. 25, No. 3, (May 1, 1977) pp. 275-287 (XP00203447).

* cited by examiner

*Primary Examiner* — Sue Liu
*Assistant Examiner* — Andriae M Holt
(74) *Attorney, Agent, or Firm* — Matthew D. Kellam

(57) ABSTRACT

The present invention generally relates to a glyphosate formulation with enhanced viscosity, said formulation containing a thickening composition comprising at least one nitrogen-containing surfactant.

9 Claims, No Drawings

THICKENING GLYPHOSATE FORMULATIONS

FIELD OF THE INVENTION

The present invention relates to a glyphosate formulations thickened by nitrogen containing surfactants.

BACKGROUND OF THE INVENTION

Glyphosate is the most widely used herbicide in the world. It is a broad spectrum herbicide, meaning it controls both narrow leaf grass and broad leaf weed. Since it has very limited solubility in water, glyphosate acid is usually first converted to a soluble salt. Examples are isopropyl amine (IPA), monoethanol amine (MEA), diethanol amine (DEA), triethanol amine (TEA), sodium (Na), potassium (K), ammonium (NH4), and trimesium.

IPA glyphosate (with some surfactants) was first commercialized as ROUNDUP® Original by Monsanto because it was relatively easy to formulate. Glyphosate formulations with other salts, in particular the ammonium and potassium, have been introduced to market recently.

Use of a concentrated aqueous formulation of glyphosate in the form of a salt made with the inorganic base ammonia and potassium is advantageous Ammonia and potassium are low in costs, readily available, low in molecular weights, and are relatively soluble in water. Additionally, they are natural nutrients for the growth of plants and other organisms.

The use of ammonium and potassium salts of glyphosate for preparing aqueous concentrate formulations of glyphosate suitable for killing and controlling plants has, however, been somewhat limited due to difficulties arising from chemical and physical properties of the ammonium and potassium salts of glyphosate, and lack of biologically suitable surfactants for preparing high-loaded liquid concentrates of such salts. If the biologically suitable surfactants are used, the surfactants tend to lack the property of thickening the glyphosate formulation to desirable viscosity even at highest glyphosate concentration allowable for a liquid formulation. The desired high viscosity in ROUNDUP® Original formulation arises mainly from the IPA as the counterion for glyphosate and not from the surfactant used in the formulation. If K and NH4 glyphosate is formulated into the same 360 g/l, the viscosity is much lower than ROUNDUP® Original. As a matter of fact, even at much higher concentration, such as 540 g/l, the viscosity of the K glyphosate formulation (e.g., ROUNDUP® WeatherMax, 45 cps/22° C.) is still lower than the viscosity of the ROUNDUP® Original (54 cps/22 ° C.). Glyphosate rates and concentrations given herein, even where the glyphosate is present as a salt or salts, are expressed as acid equivalent (ae) unless the context demands otherwise.

Because of the much lower viscosity exhibited in lower than 360 g/l in the case of IPA-glyphosate or in 360 g/l in the case of K- and NH4-glyphosate formulations, many farmers feel that they are being short changed by manufacturers in that they are receiving a watered down product.

Over the years, there has been a request from market place for a glyphosate thickener to improve formulation aesthetics. Accordingly, thick glyphosate formulations, especially the K and NH4 glyphosate formulations, are needed in the market place. However, thickening a glyphosate formulation to desired viscosity, typically 40 cps or higher, is technically challenging. For example, it has previously not been possible to thicken a K and NH$_4$ glyphosate formulation in the concentration range of 360 to 540 g/l. Gelling a glyphosate formulation presents even bigger challenges. When attempting to thicken such formulations, those skilled in the art commonly use water-soluble polymeric thickeners. However, none of the commonly used polymer thickeners works in concentrated glyphosate formulations because they lose their thickening ability as they have a tendency to separate out of solution.

Viscosity requirements vary depending on the specific application. For example, a wiper application requires the formulation to have higher viscosity. Glyphosate formulations generally have higher viscosity as the concentration of glyphosate increases. Farmers sometimes use undiluted Roundup® Original in the wick application to insure high enough viscosity to minimize dripping off. However, use of the undiluted Roundup® Original in the wick application is uneconomical as in those cases it is desirable to use a less concentrated glyphosate. However, use of less concentrated glyphosate formulations presents a potential dripping problem due to low viscosity. Therefore, there is need to thicker diluted glyphosate formulations for wick application to reduce the dripping.

During the spraying application of a dilute pesticide solution, some fine droplets have the potential to drift with wind to unintended area causing damage to the crops in the area. Farmers typically use a water soluble polymer such as guar gum as the drift control agent to control the drift. It is well known that even a small increase in viscosity (~2-3cps) caused by addition of the guar gum in the dilute pesticide solution has significant effect on drift.

The present inventors have discovered that certain classes of nitrogen containing surfactants can thicken glyphosate formulations very effectively.

SUMMARY OF THE INVENTION

The present invention generally relates to a thickened glyphosate formulation and to a method of thickening glyphosate. In accordance with the invention, glyphosate formulations are thickened by use of at least one nitrogen containing surfactant of general formula (A)-(F) as described below. The glyphosate formulation thickened in accordance with the present invention generally has an increased viscosity of 5 cps or more in the case of a concentrate or 1 cps or more in the case of a ready-to-spray solution after the addition of the at least one of the described nitrogen containing derivatives of the invention.

DETAILED DESCRIPTION OF THE INVENTION

The present invention generally relates to a thickened glyphosate formulation and to a method of thickening glyphosate. In accordance with the invention, glyphosate formulations are thickened by use of a thickening composition which comprises at least one nitrogen-containing surfactant of general formula (A)-(F) as described below.

A first class of nitrogen-containing surfactants is represented by general formula (A), below.

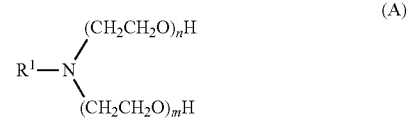

(A)

where $R^1$ is C16 to C22 linear or branched, saturated or unsaturated hydrocarbon chain, n=1-4 and m=1-4. In another embodiment n=1-2, and m=1-2. Non-limiting examples of nitrogen containing surfactants of general formula (A) include, but are not limited to tallowamine-2EO, erucicamine-2EO and mixtures thereof.

A second class of nitrogen-containing surfactants is represented by general formula (B), below.

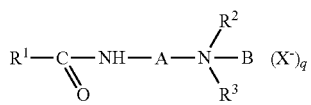

where $R^1$ is C16 to C22 linear or branched, saturated or unsaturated hydrocarbon chain; A is C1 to C6 linear or branched saturated or unsaturated hydrocarbon chain, and B is $CH_3$, O (oxygen), or $CH_2$—COO; $X^-$ is an anion including, but not limited to chloride, bromide or methylsulfate; q is 0 when B is oxygen or $CH_2$—COO or 1 when B is $CH_3$; $R^2$ and $R^3$ are independently $CH_3$ or $CH_2CH_2OH$. Non-limiting examples of compounds in accordance with formula (B) include tallow dimethylamidopropylamine oxide, erucic dimethylamidopropylamine methyl chloride quaternary, erucic dimethylamido betaine and mixtures thereof.

A third class of nitrogen-containing surfactants is represented by general formula (C), below.

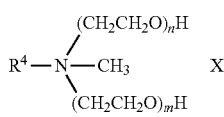

where $R^4$ is C20 to C22 linear or branched, saturated or unsaturated hydrocarbon chain; n=1-4, m=1-4; in another embodiment n=1-2, and m=1-2, and $X^-$ is an anion such as chloride, bromide or methylsulfate. A non-limiting example of a nitrogen containing surfactant according to general structure (C) is erucicamine-2EO methylchloride quaternary (i.e. Ethoquad E/12), wherein $R^4$ is C22 from erucic acid.

A fourth class of nitrogen-containing surfactants is represented by general formula (D), below.

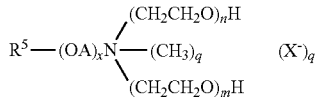

where $R^5$ is C6 to C22 linear or branched, saturated or unsaturated hydrocarbon chain; A is C1 to C6 linear or branched, saturated or unsaturated hydrocarbon chain, x=1-6, n=1-4, m=1-4, $X^-$ is an anion such as chloride, bromide or methylsulfate and q is 0 or 1. In another embodiment x=1-3, n=1-2, and m=1-2. Non-limiting examples of compounds in accordance with formula (D) are C12/13 etheramine-2EO and the quaternary ammonium product thereof.

A fifth class of nitrogen-containing surfactants is represented by general formula (E), below.

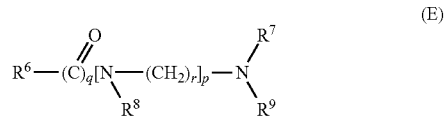

Where $R^6$ is C12-C22 or branched, saturated or unsaturated hydrocarbon chain, q=0 or 1, r=2-6, and p=0-5. $R^7$, $R^8$ and $R^9$ are each independently chosen from H, $CH_3$, $CH_2$—$CH_2$—OH, $CH_2$—COOM or $CH_2CH_2COOM$ (M is comprised of H, Na, K, or NH4) with at least one group being $CH_2$—COOM or $CH_2CH_2COOM$. Non-limiting examples of nitrogen containing surfactants in accordance with general formula (E) include, but are not limited to coco amphocarboxyglycinate ($R^6$=coco, q=1, r=2, p=1, $R^7$ is $CH_2COO$ Na, $R^8$ is H or $CH_2CH_2OH$, and $R^9$, different than $R^8$, is $CH_2CHOH$ or H), oleylampho polycarboxy glycinate ($R^6$=oleic, q=0, r=3, p=3, and $R^7$, $R^8$ and $R^9$ are $CH_2CH_2COO$ Na), and mixtures thereof.

A sixth class of nitrogen-containing surfactants is represented by general formula (F), below.

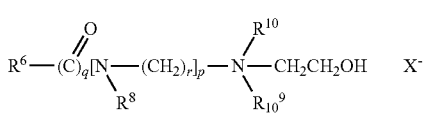

Where $R^6$ is C12-C22 or branched, saturated or unsaturated hydrocarbon chain, q=0 or 1, r=2-6, and p=0-5. $X^-$ is an anion such as acetate, nitrate, halide, methyl sulfate, or ethylsulfate. $R^{10}$ is either $CH_2CH_2OH$ or $CH_3$. Non-limiting examples of the compounds in accordance with formula (F) include tris(2-hydroxyethyl) tallowalkyl ammonium acetate and (2-hydroxyethyl) tallow dimethyl ammonium acetate.

Generally, the invention is suitable for a diluted and ready-to-spray glyphosate solution or a concentrated glyphosate formulation. The suitable glyphosate concentration of the invention is from about 0.5 to 45 wt % a.e., from about 0.5 to about 40 wt %. a.e., or from about 0.5% -30% a.e. The concentrated glyphosate formulation typically contains more than about 10% glyphosate a.e. Typically, the formulations of the present invention have a pH greater than about 4, greater than about 4.6, greater than about 4.7, greater than about 4.8, or greater than about 4.9.

The concentrated glyphosate formulation thickened in accordance with the present invention generally has an increased viscosity of 5 cps, in another embodiment an increased viscosity of 10 cps, in another embodiment an increased viscosity of 15 cps, and in yet in another embodiment an increased viscosity of 20 cps, or more after the addition of the at least one of the described nitrogen containing derivatives of the invention. The ready-to-spray glyphosate formulation thickened in accordance with the present invention generally has an increased viscosity of 1 cps, in another embodiment an increased viscosity of 2 cps, in another embodiment an increased viscosity of 3 cps, and in yet in another embodiment an increased viscosity of 5 cps, in another embodiment at least 10 cps, in another embodiment at least 15 cps, and in yet in another embodiment at least 20 cps or more after the addition of the at least one of the described nitrogen containing derivatives of the invention. More particularly, glyphosate formulations containing the thickening agent(s) of the invention in effective amounts typically exhibit increased viscosity compared to the same formulations not containing the thickening agents of the invention.

It is well known to the skilled in the art that to measure accurately the viscosity value for a sample with very low viscosity (~1.0 cp) a U-tube viscometer based on mass flow under gravity shall be used.

For application to a field for control of weeds, a typical formulation according to the invention contains glyphosate acid equivalent in the range of from about 0.5 to 3 wt. %, typically 1 to 2 wt. %. However, stronger mixtures, e.g., in the range from about 2 to about 15 wt. % surfactant may be desirable for some applications. In some special applications, a >360 g/l glyphosate formulation is used directly without further dilution.

The nitrogen containing surfactants forming the thickening adjuvant composition of the invention are either commercially available or can be manufactured by procedures known to those skilled in the art.

The thickening composition of the invention is added to said glyphosate formulation in an amount effective to thicken said formulation to the desired degree. In most cases, said effective amount is exemplified by a weight ratio of glyphosate (a.e.) to thickening composition of from about 25:1 to about 0.5:1, typically from about 20:1 to about 1:1 and, in another embodiment, from about 8:1 to about 1.5:1. In most cases, said effective amount is exemplified by a concentration range in total formulation between 0.05%-10%, preferably 0.2%-8%, or more preferably 0.5%-5%.

Thickened herbicidal formulations of the present invention can, in addition to the thickening composition/adjuvants set forth in the above formulae, contain additional components including but not limited to, additional surfactants or other additives. It is preferred that when the formulations of the invention do contain such additional components, that such additional components are substantially non-irritating to the eye, substantially non-toxic to aquatic life, and have acceptable bio-efficacy. Such additional components include surfactants such as cationic, anionic, nonionic, and amphoteric surfactants. These surfactants are disclosed in McCutcheon's Emulsifier and Detergents, North America Edition, 2006. Non-limiting examples of preferred cationic surfactants are alkoxylated alkylamine and its quaternary derivative, alkoxylated etheramine and its quaternary derivative, alkoxylated alkyl amine oxide, alkoxylated alkyl etheramine oxide, alkyl amidopropyl amine oxide, alkyl trimethyl ammonium chloride, and alkyl dimethylamidopropylamine. Non-limiting examples of preferred anionic surfactants are alkylsulfate, alkylethersulfate, alkylsulfonate, alkylsulfosuccinate, alkoxylated phosphate ester, alkyl alpha olefin sulfonate, alkyl n-methyl taurate, fatty acid isethionate, and alkyl ether carboxylate. Non-limiting examples of preferred nonionic surfactants are sorbitan ester and its alkoxylated derivative, sorbitol ester and its alkoxylated derivative, fatty acid ester, castor oil alkoxylate, alcohol alkoxylate, alkanolamide, alkanolamide alkoxylate, and alkyl polyglycoside. Non-limiting examples of preferred amphoteric surfactants are alkyl betaine, alkyl amidopropyl betaine, alkylamphoacetate, alkylamphodiacetate, alkylamphocarboxylate, alkylamphopropionate, alkylamphodipropionate, alkyl amidoamine carboxylate, alkylamphohydroxypropyl sulfonate, alkyl sultaine, alkyl amidopropyl hydroxyl sultaine, alkyl dihydroxyethyl glycinate, and alkyl aminopropionate.

The present invention encompasses not merely formulations of glyphosate, but also relates to other herbicidal compositions comprising at least one co-herbicidal active, and at least one surfactant, wherein said at least one surfactant comprises the adjuvants of the invention. An herbicidal composition according to the invention can optionally comprise other additives such as ammonium sulfate, potassium sulfate, potassium chloride, sodium sulfate, urea, glycerol, glycols, polyglycols, water soluble polymers, or mixtures thereof. A contemplated composition can optionally include one or more of the following: quick-burn additive, humectant, co-herbicide, other pesticides, other amine compounds, e.g., dimethylamine, isopropylamine, triethylamine, diethanolamine, dye, pigment, corrosion inhibitor, thickener, dispersing agent, calcium sequestrant, defoamer, antifreeze, pour-point depressant, anti-gelling agents, pH modifiers, preservatives, hydrotropes, solvents, process aids, or mixtures thereof.

Combinations of glyphosate salts and co-herbicide salts are specifically contemplated by the present invention. Preferably, additives used in glyphosate compositions of the present invention possess sufficient solubility or dispersibility in a concentrated aqueous potassium or ammonium glyphosate solution at a pH of from about 4 to about 7 to allow desired concentrations to be attained.

Where a co-herbicide is included in the formulation, it is preferred that the co-herbicide be water-soluble and will not form precipitate with the surfactants of the present invention and glyphosate, and more preferred that it be included in the form of an amine salt, sodium, ammonium or potassium salt. Examples of suitable co-herbicides are Acetochlor, Acifluorfen, Aclonifen, Alachlor, Ametryn, Amidosulfuron, Aminopyralid, Amitrole, Anilofos, Asulam, Atrazine, Azafenidin, Azimsulfuron, Benazolin, Benfluralin, Bensulfuron-methyl, Bentazone, Bifenox, Binalafos, Bispyribac-sodium, Bromacil, Bromoxynil, Butachlor, Butroxidim, Cafenstrole, Carbetamide, Carfentrazone-ethyl, Chloridazon, Chlorimuron-ethyl, Chlorobromuron, Chlorotoluron, Chlorsulfuron, Cinidon-ethyl, Cinosulfuron, Clethodim, Clomazone, Clopyralid, Cloransulam-methyl, Clorsulfuron, Cyanazine, Cycloate, Cyclosulfamuron, Cycloxydim, Dalapon, Desmedipham, Dicamba, Dichlobenil, Dichlormid, Diclosulam, Diflufenican, Dimefuron, Dimepipeate, Dimethachlor, Dimethenamid, Diquat, Diuron, Esprocarb, Ethalfluralin, Ethametsulfuron-methyl, Ethofumesate, Ethoxysulfuron, Fentrazamide, Flazasulfuron, Florasulam, Fluchloralin, Flufenacet, Flumetsulam, Flumioxazin, Fluometuron, Flupyrsulfuron-methyl, Flurochloridone, Fluroxypyr, Flurtamone, Fomesafen, Foramsulfuron, Glufosinate, Hexazinone, Imazamethabenz-m, Imazamox, mazapic, Imazapyr, Imazaquin, Imazethapyr, Imazosulfuron, Iodosulfuron, Ioxynil, Isoproturon, Isoxaben, Isoxaflutole, Lactofen, Lenacil, Linuron, Mefenacet, Mesosulfuron-Methyl, Mesotrione, Metamitron, Metazachlor, Methabenzthiazuron, Metobromuron, Metolachlor, Metosulam, Metoxuron, Metribuzin, Metsulfuron-methyl, Molinate, MSMA, Napropamide, Nicosulfuron, Norflurazon, Oryzalin, Oxadiargyl, Oxadiazon, Oxasulfuron, Oxyfluorfen, Paraquat, Pendimethalin, Phenmedipham, Picloram, Pretilachlor, Profoxydim, Prometryn, Propanil, Propisochlor, Propoxycarbazone, Propyzamide, Prosulfocarb, Prosulfuron, Pyraflufen-ethyl, Pyrazosulfuron, Pyridate, Pyrithiobac, Quinclorac, Quinmerac, Rimsulfuron, Sethoxydim, Simazine, S-Metolachlor, Sulcotrione, Sulfentrazone, Sulfosulfuron, Tebuthiuron, Tepraloxydim, Terbuthylazine, Terbutryn, Thifensulfuronmethyl, Thiobencarb, Tralkoxydim, Tri-allate, Triasulfuron, Tribenuron-methyl, Triclopyr, Trifloxysulfuron, Trifluralin, Triflusulfuron-methyl, Tritosulfuron, and mixtures and combinations thereof. More preferred co-herbicides are Acetochlor, Aminopyralid, Amitrole, Atrazine, Bensulfuron-methyl, Bromoxynil, Chlorimuron-ethyl, Clethodim, Clomazone, Dicamba, Dimethenamid, Flumetsulam, Glyfosinate, Imazethapyr, Imazamox, Isoproturon, Isoxaflutole, Mesotrione, Metamitron, Metosulam, Metsulfuron-methyl, Nicosulfuron, Paraquat, Pendimethalin, Picloram, Propanil, Rimsulfuron, S-Metolachlor, Tribenuron-methyl, Triclopyr, Trifluralin, and mixtures and combinations thereof. The most preferred co-herbicides are 2,4-D, Atrazine, Aminopyralid, Amitrole, Bensulfuron-methyl, Dicamba, Flumetsulam, Glyfosinate, Imazamox, Isoproturon, Metosulam, Metsulfuron-methyl, Nicosulfuron, Pendimethalin, Rimsulfuron, Tribenuron-methyl, and mixtures and combinations thereof. In various advantageous embodiments, the formulation comprises a co-herbicide selected from the group consisting of diuron, fluometuron, prometryn, and combinations thereof.

Further in accordance with the present invention, the formulation may comprise a co-herbicide selected from the group consisting of 4-chlorophenoxyacetic acid (4-CPA) or a salt thereof, 2,4-dichlorophenoxyacetic acid (2,4-D) or a salt thereof, 3,4-dichlorophenoxyacetic acid (3,4-DA) or a salt thereof, 4-chloro-2-methylphenoxyacetic acid (MCPA) or a salt thereof, 2,4,5-trichlorophenoxyacetic acid (2,4,5-T) or a salt thereof, 2-(3-chlorophenoxy)propanoic acid (cloprop) or a salt thereof, 2-(4-chlorophenoxy)propanoic acid (4-CPP) or a salt thereof, 2-(2,4-dichlorophenoxy)propanoic acid (dichlorprop) or a salt thereof, 2-(3,4-dichlorophenoxy)propanoic acid (3,4-DP) or a salt thereof, 2-(2,4,5-trichlorophenoxy)propanoic acid (fenoprop) or a salt thereof, 2-(4-chloro-2-methylphenoxy)propanoic acid (mecoprop) or a salt thereof, 4-(4-chlorophenoxy)butanoic acid (4-CPB) or a salt thereof, 4-(2,4-dichlorophenoxy)butanoic acid (2,4-DB) or a salt thereof, 4-(3,4-dichlorophenoxy)butanoic acid (3,4-DB) or a salt thereof, 4-(4-chloro-2-methylphenoxy)butanoic acid (MCPB) or a salt thereof, 4-(2,4,5-trichlorophenoxy)butanoic acid (2,4,5-TB) or a salt thereof, 3-amino-2,5-dichlorobenzoic acid (chloramben) or a salt thereof, 3,6-dichloro-2-methoxybenzoic acid (dicamba) or a salt thereof, 2,3,6-trichlorobenzoic acid (2,3,6-TBA) or a salt thereof, 2,3,5-trichloro-6-methoxybenzoic acid (tricamba) or a salt thereof, 4-amino-3,6-dichloro-2-pyridinecarboxylic acid (aminopyralid) or a salt thereof, 3,6-dichloro-2-pyridinecarboxylic acid (clopyralid) or a salt thereof, 4-amino-3,5,6-trichloro-2-pyridinecarboxylic acid (picloram) or a salt thereof, 3,5,6-trichloro-2-pyridinyl)oxyacetic acid (triclopyr) or a salt thereof, and combinations thereof.

Regardless of the particular co-herbicide, or combination of co-herbicides present in the formulation, the weight ratio of glyphosate (a.e.) to one or more co-herbicides is typically from about 0.5 to about 4.0 and, still more typically, from about 1.0 to about 2.0.

Formulations of the present invention may be generally prepared by mixing the glyphosate salt solution, prepared as outlined above, together with other ingredients in a suitable mixing vessel with agitation, such as a blender.

This invention also relates to an herbicidal method of using a contemplated composition in an amount effective to kill or control unwanted vegetation by either diluting an aqueous concentrate composition in water to provide a diluted mixture for application or applying directly the concentrate without further dilution to foliage of the vegetation to be killed or controlled. The glyphosate formulation of the invention should be applied to plant foliage at an application rate sufficient to give the desired effect. Application rates are usually expressed as amount of glyphosate ae per unit area of land treated, e.g. grams ae per hectare (g ae/ha). What constitutes a "desired effect" varies according to the standards and practice of those who investigate, develop, market, and use glyphosate products. For example, the amount of glyphosate ae applied per unit area to give, consistently and reliably, at least 85% control of a plant species as measured by growth reduction or mortality is often used to define a commercially effective rate.

Preferred compositions of the invention provide equivalent herbicidal efficacy by comparison with commercial standard formulations of glyphosate "Herbicidal efficacy," as used herein, refers to any observable measure of control of plant growth, which can include one or more of the actions of (1) killing, (2) inhibiting growth, reproduction or proliferation, and (3) removing, destroying, or otherwise diminishing the occurrence and activity of plants.

The selection of application rates that are biologically effective for a specific glyphosate formulation, such as a formulation of the present invention, is within the skill of the ordinary agricultural scientist. Those skilled in the art will likewise recognize that individual plant conditions, weather, and growing conditions, as well as the specific formulation selected, will influence the degree of biological effectiveness achieved in practicing this invention. Useful application rates can therefore depend upon all of the above conditions. Much information is known about appropriate application rates for glyphosate formulations in general. Over two decades of glyphosate use and published studies relating to such use have provided abundant information from which a weed control practitioner can select glyphosate application rates that are herbicidally effective on particular species at particular growth stages in particular environmental conditions.

Various application methods may be employed including broadcast spraying, directed spraying or wiping the foliage with a diluted composition or a concentrate of this invention. Depending on the degree of control desired, the age and species of the plants, weather conditions and other factors, typically the glyphosate application rate is an herbicidally effective amount of about 0.1 to about 10 kg ae/ha and preferably from about 0.25 to about 2.5 kg ae/ha, although greater or lesser amounts may be applied.

The invention will now be illustrated by the following non-limiting examples.

EXAMPLES

Anionic and nonionic surfactants and commonly used polymer thickeners did not showed significant thickening property in concentrated glyphosate formulations.

It was unexpectedly discovered that certain nitrogen containing surfactants thickened glyphosate formulations very effectively. Non-limiting examples are Ethomeen T/12, Ethomeen S/12, C12/13 etheramine-2EO, Aromox APA-T, Arquad APA-E E, Ethoquad E/12, (i.e., erucicamine-2EO methylchloride quaternary), Erucic DMAPA betaine, Ampholak XO7/C, Ampholak XCO-30, tris(2-hydroxyethyl) tallowalkyl ammonium acetate, and (2-hydroxyethyl) tallow dimethyl ammonium acetate.

Example 1

| | #1 | #2 | #3 | #4 | #5 | #6 | #7 | #8 |
|---|---|---|---|---|---|---|---|---|
| Viscosity of 23.2 wt % a.i. K-glyphosate + Thickener + water | | | | | | | | |
| K-glyphosate | 23.3 | 23.2 | 23.2 | 23.2 | 23.2 | 23.2 | 23.2 | 23.3 |
| Arquad APA-E E (Erucic DMAPA Quat) | 0.14 | 0.52 | | | | | | |
| Aromox APA-T (Tallow DMAPA oxide) | | | 3.0 | | | | | |
| Ethomeen SV/12 (Soyamine-2EO) | | | | 10 | | | | |
| Ethomeen C/12 (Cocoamine-2EO) | | | | | 10 | | | |
| Ethomeen SV/15 (Soyamine-5EO) | | | | | | 10 | | |
| Erucic DMAPA Betaine | | | | | | | 0.5 | |
| Ethoquad E/12 | | | | | | | | 0.5 |
| Naxonate 4LS (40% SXS) | 1.09 | 1.05 | | | | | | |
| Water | 75.47 | 75.13 | 73.7 | 66.7 | 66.7 | 66.7 | 76.3 | 76.3 |
| Viscosity, cps* (20 rpm/22° C.) | 58** | 122** | 417 | 44 | <6 | <6 | Thick hazy | Thick clear |

*Brookfield viscometer.
**Behaved like egg-white.

It can be seen in this example that soyamine-2EO at 10%, erucic-2EO quat at 0.5%, Erucic DMAPA quat at 0.14%, Erucic DMAPA betaine at 0.5% and tallow DMAPA oxide at 3% thickened the K-glyphosate solution to desirable viscosity. On the other hand, Cocoamine-2EO and soyamine-5EO, though structurally similar to the soyamine-2EO, did not show thickening ability at 10% surfactant concentration.

All formulations in this example were stable between 0° C. and 40° C.

Example 2

| Thickener | Description of Thickener | Wt % of Thickener | Viscosity (cps) @ 22° C. | @ 2° C. |
|---|---|---|---|---|
| Viscosity of 37.34 wt % a.i. K-glyphosate + thickener + water (to 100%). (20 rpm) | | | | |
| Ethomeen SV/12 | Soyamine-2EO | 1.00 | 15 | |
| | | 2.00 | 42 | 32 |
| | | 3.00 | 259 | |
| | | 4.00 | 1581 | |
| | | 5.20 | viscous | |
| Ampholak XCO-30 | Na Cocoampho carboxy glycinate 30% | 2.00 | 55 | 28 |
| | | 5.20 | 553 | |
| | | 10.00 | 1791 | |
| Aromox APA-T | Tallow DMAPA oxide | 3.00 | Clear gel | |
| Ethoduomeen C/13 | Coco diamine-3EO | 5.20 | thin | |
| Ethomeen T/15 | Tallowamine-5EO | 5.20 | 9 | |
| Ethoquad T/12 | Tallowamine-2EO MeCl | 5.20 | thin | |
| Ethoquad T/15 | Tallowamine-5EO MeCl | 5.20 | thin | |
| Ethotetrameen T/15 | Tallow tetramine-5EO | 5.20 | thin | |
| Ethomeen C/12 | Cocoamine-2EO | 5.20 | 9 | |
| Ethomeen T/20 | Tallowamine-10EO | 5.20 | 9 | |
| Ampholak 7CX/C | Cocoampho polycarboxy glycinate 40% | 15.00 | thin | |
| Ampholak XO7/C | Oleylampho polycarboxy glycinate 40% | 15.00 | 7 | |
| Ampholak YJH-40 | Octyl iminodipropionate 40% | 15.00 | thin | |
| Amphoteen 24 | Lauryldimethyl betaine 30% | 15.00 | 21 | |
| Water | Water | 5.20 | 6 | |

It can be seen in this example that, at relatively low concentration of 2%, soyamine-2EO and sodium cocoamphocarboxy glycinate thickened K-glyphosate solution dramatically to a desirable viscosity. An amine oxide, exemplified by tallow DMAPA oxide, gelled K-glyphosate formulation at only 3%.

On the other hand, cocoamine-2EO, tallowamine-5EO and 10EO, tallowamine-2EO and 5EO quats, polyamine ethoxylates (cocodiamine-3EO and tallow tetramine-5EO), though structurally similar to the soyamine-2EO, did not show thickening ability in this system. With 1% soyamine-2EO, the viscosity of K-glyphosate formulation was 15 cps which was already higher than the viscosity of 9 cps achieved with 5.2% cocoamine-2EO or tallowamine-5EO.

Cocoampho polycarboxy glycinate, oleylampho polycarboxy glycinate, octyl iminodipropionate, and Lauryldimethyl betaine, though showed very similar physical properties to the sodium cocoamphocarboxy glycinate in many applications, did not show thickening ability in this system. With 2% sodium cocoamphocarboxy glycinate (30%), the viscosity of the K-glyphosate formulation was 55 cps which was already much higher than the viscosity (7 cps or less) achieved with 15% cocoampho polycarboxy glycinate (40%), oleylampho polycarboxy glycinate (40%), or octyl iminodipropionate (40%), or lauryldimethyl betaine (30%).

All formulations in this example were stable between 0° C. and 40° C.

Example 3

| Viscosity of 48.9% K-glyphosate + 10% Thickeners + water (to 100%) | | | | | | |
|---|---|---|---|---|---|---|
| | #1 | #2 | #3 | #4 | #5 | #6 |
| K-glyphosate, wt % a.i. | 58 | 48.9 | 48.9 | 48.9 | 48.9 | 48.9 |
| Water, wt % | 42 | 51.1 | 41.1 | 41.1 | 41.1 | 41.1 |
| Ethomeen T/16 (Tallowamine-6 EO), wt % | | | | | | 10 |
| Ethomeen C/12 (Cocamine-2 EO), wt % | | | | | 10 | |
| Ethomeen T/12 (Tallowamine-2 EO), wt % | | | 10 | | | |
| Ethomeen EA-1213/12 (C1213 etheramine-2 EO), wt % | | | | 10 | | |
| Viscosity, cps (20 rpm/22° C.) | 60 | 16 | Gel | Gel | 65 | Separated |

All formulations in this example were stable between 0° C. and 40° C. except for #6. The data show that at 58% and 48.9% solids, the glyphosate formulation had a viscosity of 60 cps and 16 cps, respectively (#1 and #2).

When about 9% K-glyphosate solid and 1% water in formulation #1 were replaced by 10% tallowamine-2EO or C12/13 etheramine-2EO, the formulations (#3 and #4) became clear gels.

However, when about 9% K-glyphosate solid and 1% water in formulation #1 were replaced by 10% cocoamine-2, which is structurally similar to tallowamine-2EO and C1213 etheramine-2EO, the formulation viscosity (#5) remained relatively unchanged.

Moreover, when about 9% K-glyphosate solid and 1% water in formulation #1 were replaced by 10% tallowamine-6EO, which is structurally similar to tallowamine-2EO, the formulation (#6) became unstable and separated at room temperature.

This example suggested that in order for a surfactant to be able to thicken a glyphosate formulation, the surfactant should be compatible in the glyphosate system, as a necessary condition. However, not all compatible surfactants possess the ability to thicken glyphosate.

Example 4

| Viscosity of IPA, K and NH4-glyphosate + Amphoteric Surfactants + water (to 100%) | | | | | | |
|---|---|---|---|---|---|---|
| Wt % a.i. | Glyphosate | Ampholak 7CX/C | Ampholak XO7/C | Ampholak YJH-40 | Ampholak XCO-30 | Room Temp |
| 55.8 | IPA-glyp | 10 | | | | clr |
| 49.6 | IPA-glyp | 20 | | | | clr |
| 43.4 | IPA-glyp | 30 | | | | clr |
| 55.8 | IPA-glyp | | 10 | | | clr |
| 49.6 | IPA-glyp | | 20 | | | clr |
| 43.4 | IPA-glyp | | 30 | | | clr |
| 55.8 | IPA-glyp | | | 10 | | clr |
| 49.6 | IPA-glyp | | | 20 | | clr |
| 43.4 | IPA-glyp | | | 30 | | clr |
| 55.8 | IPA-glyp | | | | 10 | Clr, viscous |
| 49.6 | IPA-glyp | | | | 20 | Clr, viscous |
| 43.4 | IPA-glyp | | | | 30 | Clr, viscous |
| 52.2 | K-glyp | 10 | | | | clr |
| 46.4 | K-glyp | 20 | | | | clr |
| 40.6 | K-glyp | 30 | | | | clr |
| 52.2 | K-glyp | | 10 | | | clr |
| 46.4 | K-glyp | | 20 | | | clr |
| 40.6 | K-glyp | | 30 | | | slight hazy |
| 52.2 | K-glyp | | | 10 | | very hazy |
| 46.4 | K-glyp | | | 20 | | hazy/sep |
| 40.6 | K-glyp | | | 30 | | hazy/sep |
| 52.2 | K-glyp | | | | 10 | very hazy |
| 46.4 | K-glyp | | | | 20 | hazy/sep |
| 40.6 | K-glyp | | | | 30 | clear gel |
| 45 | NH4-glyp | 10 | | | | clr |
| 40 | NH4-glyp | 20 | | | | clr |
| 35 | NH4-glyp | 30 | | | | clr |
| 45 | NH4-glyp | | 10 | | | clr gel |
| 40 | NH4-glyp | | 20 | | | clr |
| 35 | NH4-glyp | | 30 | | | clr |
| 45 | NH4-glyp | | | 10 | | clr |
| 40 | NH4-glyp | | | 20 | | clr |
| 35 | NH4-glyp | | | 30 | | clr |
| 45 | NH4-glyp | | | | 10 | very hazy |
| 40 | NH4-glyp | | | | 20 | hazy/sep |
| 35 | NH4-glyp | | | | 30 | hazy gel |

The data show that Ampholak XCO-30 and XO7/C had the ability to thicken glyphosate formulations. However, their thickening ability was very sensitive to the counter ions of glyphosate Ampholak XO7/C, which showed the ability to gel NH4-glyphosate, did not show the ability to gel K-glyphosate. On the other hand, Ampholak XCO-30 showed that the gel could only be obtained with certain concentration range.

Moreover, Ampholak 7CX/C and YJH-40, structurally similar to Ampholak XCO-30 and XO7/C, didn't showed significant thickening ability in glyphosate formulations.

Example 5

| | #1 | #2 | #3 | #4 |
|---|---|---|---|---|
| K-glyphosate | 18 | 16.45 | 36 | 2.47 |
| Water | 77.16 | 80.98 | 54 | 93.26 |
| Tris(2-hydroxyethyl) tallowalkyl ammonium acetate (27%) | 4.5 | 2.39 | 9 | |
| (2-hydroxyethyl) tallow dimethyl ammonium acetate (80.3%) | | | | 3.32 |

-continued

|  | #1 | #2 | #3 | #4 |
|---|---|---|---|---|
| Sodium salicylate | 0.34 | 0.18 | | |
| Sodium xylene sulfonate (40%) | | | 1 | 0.95 |
| Appearance at room temperature | Clear gel | Clear viscous | Clear gel | Clear viscous |

The data show that tris(2-hydroxyethyl) tallowalkyl ammonium acetate and (2-hydroxyethyl) tallow dimethyl ammonium acetate had the ability to thicken glyphosate formulations at high and low glyphosate concentrations.

The data in the above examples (1-5) demonstrate that nitrogen containing surfactants have the ability to thicken glyphosate formulations. However, it seems there was no logic behind the thickening ability of the surfactants in glyphosate system. It is difficult to predict the thickening property even within a family of surfactants. For example, tallowamine-2EO (and soyamine-2EO), erucid-2EO quat and C12/13 etheramine-2EO are much better thickeners compared to structurally similar cocoamine-2EO, talloamine-5EO, tallowamine-2EO quat, and tallow polyamine ethoxylates. Regarding the amphoteric surfactants studied, Ampholak XCO-30 (sodium cocoampho carboxy glycinate) and Ampholak XO7/C (oleylampho polycarboxy glycinate or sodium carboxymethyl oleyl polypropylamine) were found to be effective thickeners while lauryldimethylbetaine, Ampholak 7CX/C (cocoampho polycarboxy glycinate) and Ampholak YJH-40 (octyl iminodipropionate) were not.

I claim:

1. A method of thickening a glyphosate formulation which comprises adding to said formulation a thickening effective amount of a thickening composition for the purpose of thickening the glyphosate formulation, wherein the thickening composition comprises at least one nitrogen containing surfactant of formula

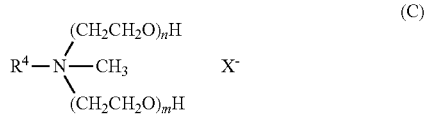

(C)

where $R^4$ is a linear or branched, saturated or unsaturated hydrocarbon chain having an average of about 22 carbon atoms derived from erucic acid; n=1-4, m=1-4, and $X^-$ is an anion.

2. The method of claim 1 characterized in that said glyphosate formulation has an increased viscosity of 5 cps or more in a concentrate with about 10% or more glyphosate or at least 1 cps in a ready-to-spray solution after the addition of the thickening composition.

3. The method of claim 1, further comprising the step of adding to the formulation a sulfonate derivative, an alkyl alpha olefin sulfonate, an alkyl alpha olefin salicylate, or mixtures thereof.

4. The method of claim 3, wherein the sulfonate derivative is sodium xylene sulfonate.

5. The method of claim 1 wherein the concentration of said thickening composition is from 0.05 to 10% by weight based on the weight of the thickened glyphosate formulation.

6. The method of claim 1 wherein n is 1 or 2, and m is 1 or 2.

7. The method of claim 1, wherein $X^-$ is an anion selected from the group consisting of chloride, bromide, and methylsulfate.

8. The method of claim 1 wherein the concentration of glyphosate in the thickened glyphosate formulation is from 0.5% to 45% ae.

9. The method of claim 1 wherein said thickening composition comprises erucicamine-2EO methylchloride quaternary.

* * * * *